United States Patent [19]

Mao

[11] B 3,983,139
[45] Sept. 28, 1976

[54] 3-(HYDROXYHYDROCARBYLSECON-DARYAMINO)THIOPHENE 1,1-DIOXIDES AND POLYURETHANES CHAIN EXTENDED THEREWITH

[75] Inventor: Chung-Ling Mao, Sandy Hook, Conn.

[73] Assignee: Uniroyal Inc., New York, N.Y.

[22] Filed: Feb. 24, 1975

[21] Appl. No.: 552,498

[44] Published under the second Trial Voluntary Protest Program on January 13, 1976 as document No. B 552,498.

Related U.S. Application Data

[62] Division of Ser. No. 434,470, Jan. 18, 1974, Pat. No. 3,887,503.

[52] U.S. Cl. ............................................. 260/330.5
[51] Int. Cl.$^2$..................................... C07D 333/66

[58] Field of Search ................................. 260/330.5

[56] References Cited
UNITED STATES PATENTS

| | | | |
|---|---|---|---|
| 2,553,495 | 5/1950 | Avakian et al.................... | 260/330.5 |
| 3,887,503 | 6/1975 | Mao ............................... | 260/2.5 AM |

Primary Examiner—Henry R. Jiles
Assistant Examiner—C. M. S. Jaisle
Attorney, Agent, or Firm—James J. Long

[57] ABSTRACT

Chain extended polyurethanes are prepared, using certain 3-(hydroxyhydrocarbylsecondaryamino)thiophene 1,1-dioxides, some of which are new chemicals. E.g., 3-(2-hydroxypropylamino)tetrahydrothiophene 1,1-dioxide is especially useful as a chain extender for high resiliency, flexible polyurethane foams.

7 Claims, No Drawings

3-(HYDROXYHYDROCARBYLSECONDARYAMINO)THIOPHENE 1,1-DIOXIDES AND POLYURETHANES CHAIN EXTENDED THEREWITH

This is a division of application Ser. No. 434,470, filed Jan. 18, 1974 now U.S. Pat. No. 3,887,503, patented June 3, 1975.

This invention relates to chain-extended polyurethanes, a method of making same, and certain new chain extenders useful in said method.

U.S. Pat. No. 2,460,955, Mortenson, Feb. 8, 1949, discloses a mixture, described as useful as a plasticizer for polyvinyl alcohol, and presumed to include 3-(2-hydroxyethylamino)thiolane-1,1-dioxide. The latter may also be called, according to the nomenclature used herein, 3-(2-hydroxyethylamino)tetrahydrothiophene 1,1-dioxide, and would have the formula:

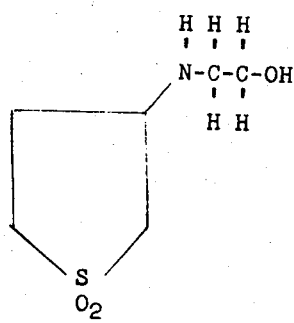

The foregoing chemical is a homolog of certain chemicals of the present invention, but is not taught as useful for chain-extending polyurethanes.

U.S. Pat. No. 3,093,793, Loev, July 23, 1963, discloses certain sulfolane solvents for pharmaceutical compositions. The chemicals of Loev are not taught as useful for chain-extending polyurethanes; the specific chemicals shown are not bifunctional and therefore would not function as chain extenders, unlike the bifunctional chemicals of the present invention.

In the manufacture of polyurethanes (long chain polyol-polyisocyanate reaction products) it is of course conventional to employ a "chain extender" which is ordinarily a poly-functional organic compound having two or more reactive hydrogen atoms (reactive toward isocyanate; as determined by what is known as the Zerewitinoff method) as an aid in building up a polyurethane molecular structure having desirable properties. In practice, the requirements of a chain extender can be quite complex and exacting, and unfortunately many of the conventional ones suffer from various shortcomings in at least certain respects. One widely used chain extender is carcinogenic. To obviate this and other disadvantages there has accordingly been a continuing search by those skilled in the art for new chain extending agents.

In accordance with the invention chain extended polyurethanes are prepared using as the chain extending agent a 3-(hydroxyhydrocarbylsecondaryamino)-thiophene 1,1-dioxide of the following formulas I or II:

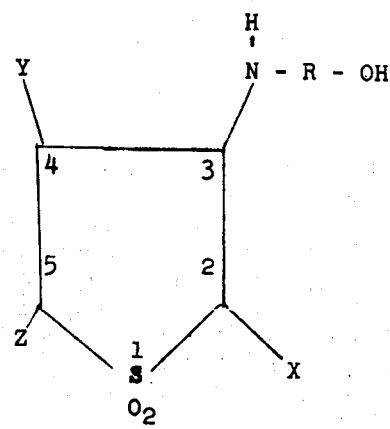

wherein
X may be hydrogen, an alkyl group having 1 to 5 carbon atoms or a halogen atom,
Y may be hydrogen, an alkyl group having 1 to 5 carbon atoms, or an aryl group,
Z may be hydrogen, an alkyl group having 1 to 5 carbon atoms, an aryl group or a halogen atom,
R may be (1) an open chain aliphatic group having 2 to 10 carbon atoms, (2) an open chain aliphatic group having 2 to 10 carbon atoms substituted with one or more aryl groups, or (3) a cycloaliphatic group having 4 to 8 carbon atoms,
the hydroxyl group being attached to a carbon atom of R that is separated from the secondary amino nitrogen atom by at least one carbon atom;

Formula II:

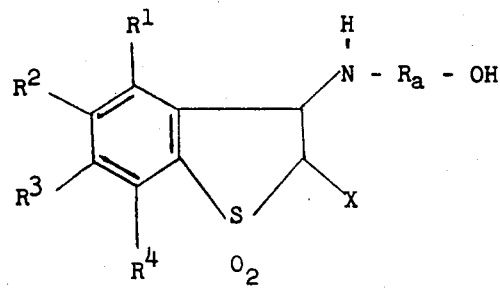

wherein
X may be as defined in formula I,
$R_a$ may be (1) an open chain aliphatic group having 2 to 10 carbon atoms, (2) an open chain aliphatic group having 2 to 10 carbon atoms substituted with one or more aryl groups, or (3) a cycloaliphatic group having 4 to 8 carbon atoms,
the hydroxyl group being attached to a carbon atom of $R_a$ that is separated from the secondary amino nitrogen atom by at least one carbon atom, and
$R^1$, $R^2$, $R^3$ and $R^4$ may be the same or different and may be hydrogen, an alkyl group having 1 to 5 carbon atoms, or halogen.

Certain of the foregoing 3-(hydroxyhydrocarbylsecondaryamino)thiophene 1,1-dioxides are new chemicals, namely, those of Formula I further embodying the proviso that when R is the group

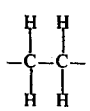

then at least one of X, Y or Z must be other than hydrogen, and those of Formula II.

The heterocyclic (hydroxyhydrocarbylsecondaryamino) thiophene dioxides of the foregoing formulas are suprisingly useful as chain extenders for polyurethanes and specifically for polyurethane foams which unexpectedly exhibit a unique combination of physical properties such as high tensile strength, high tear resistance, high elongation, good resilient properties and low compression set.

The chemicals represented by Formula I, that is, the 3-(hydroxyhydrocarbylsecondaryamino)tetrahydrothiophene 1,1-dioxides, find their greatest utility specifically in making polyurethane foam by the so-called "one-shot" method, while the chemicals represented by Formula II, that is, the 3-(hydroxyhydrocarbylsecondaryamino) dihydrobenzo[b]thiophene 1,1-dioxides, are useful not only in making one-shot foams, but also in making solid polyurethane elastomers and thermoplastics, for example from castable prepolymers, as well as coatings, etc.

The chain extending agents having Formula I may be made by a one-step synthesis starting with the known 4,5-dihydrothiophene 1,1-dioxides III according to the following scheme (wherein the symbols have the meanings previously assigned):

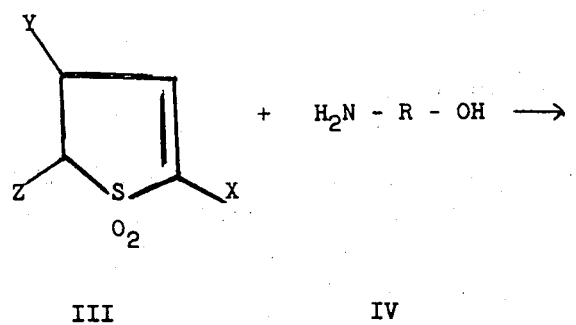

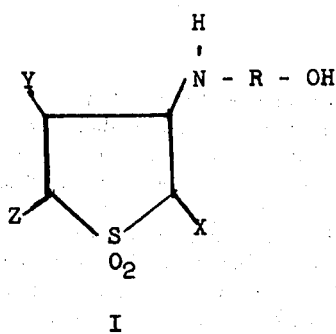

In this reaction, the 3-(hydroxyhydrocarbylsecondaryamino)tetrahydrothiophene 1,1-dioxides I are formed by reacting a 4,5-dihydrothiophene 1,1-dioxide III with the appropriate monohydroxyhydrocarbylamine IV in a suitable solvent.

Similarly, the 3-(hydroxyhydrocarbylsecondaryamino)-2,3-dihydrobenzo[b]thiophene 1,1-dioxide chain extenders having Formula II may be made by reacting a known benzo[b]thiophene dioxide V with an appropriate monohydroxyhydrocarbylamine VI in a suitable solvent according to the following scheme (the symbols being as previously defined):

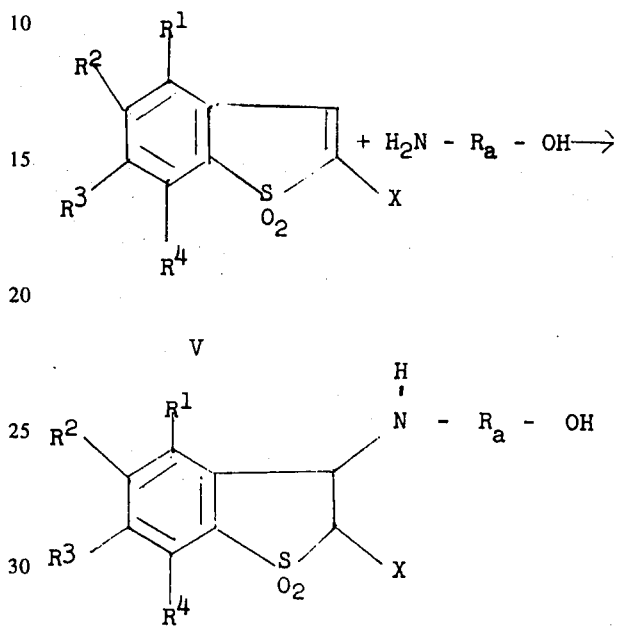

In general, one mole of the thiophene dioxide is reacted with 1.1 moles of the monohydroxyhydrocarbylamine. The reaction temperature is generally kept at 30°–120°C. and the reaction times will vary from 2 to 24 hours depending upon the thiophene dioxide and the amine employed. The reaction solvents used in this reaction are water, alcohol-water mixtures and alcohols. Examples of alcohols that may be employed include methanol, ethanol, propanol, isopropanol, pentanol, hexanol and cyclohexanol. The monohydroxyhydrocarbylamines themselves may also be used as solvents as for example, ethanolamine, propanolamine, butanolamine, hexanolamine and the like.

Any of the 4,5-dihydrothiophene 1,1-dioxides having the following general formula may be used as the starting material III for making the tetrahydrothiophene 1,1-dioxides (wherein the symbols are as defined above):

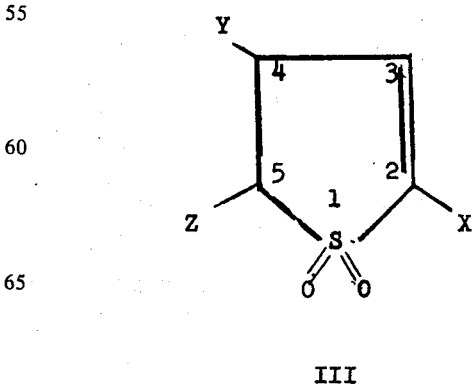

Exemplary of such thiophene dioxides are 4,5-dihydrothiophene 1,1-dioxide, 2-methyl-4,5-dihydrothiophene 1,1-dioxide, 2-chloro-4,5-dihydrothiophene 1,1-dioxide, 2-bromo-4,5-dihydrothiophene 1,1-dioxide, 2,5-dimethyl-4,5-dihydrothiphene 1,1-dioxide, 2-ethyl-4,5-dihydrothiophene 1,1-dioxide, 2-chloro-4-methyl-dihydrothiophene 1,1-dioxide, 4-phenyl-4,5-dihydrothiophene 1,1-dioxide, 2-chloro-4-phenyl-4,5-dihydrothiophene 1,1-dioxide, 2,5,5-trichloro-4,5-dihydrothiophene 1,1-dioxide, 2-bromo-4,5-diethyl-4,5-dihydrothiophene 1,1-dioxide, 2-bromo-5-phenyl-4,5-dihydrothiophene 1,1-dioxide, 2-chloro-5-butyl-4,5-dihydrothiophene 1,1-dioxide, 2-bromo-4-isopropyl-4,5-dihydrothiophene 1,1-dioxide, 4,5-dipropyl-4,5-dihydrothiophene 1,1-dioxide, 2,4-dimethyl-4,5-dihydrothiophene 1,1-dioxide, 2,5-diphenyl-4,5-dihydrothiophene 1,1-dioxide, 4,5,5-trimethyl-4,5-dihydrothiophene 1,1-dioxide, 4-ethyl-4,5-dihydrothiophene 1,1-dioxide, 5,5-dimethyl-4,5-dihydrothiophene 1,1-dioxide, and the like.

Any of the benzo[b]thiophene 1,1-dioxides having the following general formula may be used as the starting material V for making the 3-(hydroxyhydrocarbylsecondaryamino)-2,3-dihydrobenzo[b]thiophene 1,1-dioxides II (wherein the symbols are as defined above):

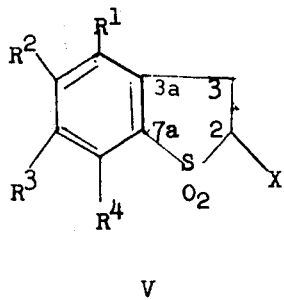

V

Exemplary of such benzo[b]thiophene 1,1-dioxides are benzo[b]thiophene 1,1-dioxide, 2-chlorobenzo[b]thiophene 1,1-dioxide, 2-bromobenzo[b]thiophene 1,1-dioxide, 2-methylbenzo[b]thiophene 1,1-dioxide, 6-butylbenzo[b]-thiophene 1,1-dioxide, 2-chloro-4-methylbenzo[b]thiophene 1,1-dioxide, 2-bromo-5,6-dimethylbenzo[b]thiophene 1,1-dioxide, 4,5,6,7-tetrachlorobenzo[b]thiophene 1,1-dioxide, 4,5,6,7-tetramethylbenzo[b]thiophene 1,1-dioxide, 2-bromo-4-chloro-6-ethylbenzo[b]thiophene 1,1-dioxide, 2-chloro-4,6-dibromobenzo[b]thiophene 1,1-dioxide, 5-tertiarybutylbenzo[b]thiophene 1,1-dioxide, 2-chloro-6-propylbenzo[b]-thiophene 1,1-dioxide, 5-chlorobenzo[b]thiophene 1,1-dioxide, 2-ethyl-5-bromobenzo[b]thiophene 1,1-dioxide, 5-pentylbenzo[b]thiophene 1,1-dioxide, and the like. Outstanding results are obtained with benzo[b]thiophene 1,1-dioxide.

Any monohydroxyhdyrocarbylamine having the following general formulas IV and VI (wherein R and $R_a$ are as defined above) may be used:

H$_2$N — R — OH        IV
H$_2$N — R$_a$— OH        VI

Exemplary of such hydroxyhydrocarbylamines are
2-hydroxyethlamine,
2-hydroxypropylamine,
2-hydroxy-2-propylamine,
3-hydroxypropylamine,
4-hydroxybutylamine,
3-hydroxybutylamine,
(3-hydroxy-1-methyl)propylamine,
(2-hydroxymethyl)-2-propylamine,
(1-hydroxymethyl-1-methyl)propylamine,
(3-hydroxy-2,3-dimethyl-1-ethyl)propylamine,
(4-hydroxy-1,1-dimethyl)butylamine,
5-hydroxypentylamine,
2-hydroxylbutylamine,
(2-hydroxyl-1-methyl)butylamine,
3-hydroxypentylamine,
4-hydroxypentylamine,
2-hydroxypentylamine,
6-hydroxyhexylamine,
4-hydroxycyclohexylamine,
(2-hydroxy-2-phenyl)ethylamine,
(2-hydroxy-2-phenyl)propylamine,
(3-hydroxy-2-phenyl)propylamine,
(2-hydroxy-2-phenyl-1-methyl-1-ethyl)ethylamine,
(5-hydroxy-1,5-dimethyl)hexylamine, and the like.

By way of non-limiting example, there may be mentioned as typical of the materials useful as chain extenders in the present invention such chemicals as 3-(2-hydroxyethylamino)-5-chloro-tetrahydrothiophene 1,1-dioxide, 3-(4-hydroxycyclohexylamino)-4,5-diphenyltetrahydrothiophene 1,1-dioxide, 3-(2-hydroxy-1-phenylethylamino)-5-methyltetrahydrothiophene 1,1-dioxide, 3-(5-hydroxypentylamino)-4-phenyl-5-bromo-2-methyltetrahydrothiophene 1,1-dioxide, 3-(4-hydroxycyclohexylamino)-2-pentyl-5-phenyltetrahydrothiophene 1,1-dioxide, 3-(10-hydroxydecylamino)-2,5-dichloro-4-pentyltetrahydrothiophene 1,1-dioxide, 3-(3-hydroxy-3-phenylpropylamino)-5-pentyl-4-methyltetrahydro-thiophene 1,1-dioxide, 3-(6-hydroxyhexylamino)-2-bromo-4-phenyl-5-propyltetrahydro-thiophene 1,1-dioxide, 3-(2-hydroxypropylamino)-2-propyl-4-phenyltetrahydrothiophene 1,1-dioxide, 3-(3-hydroxycyclohexylamino)-2,5-dibromo-4-propyltetrahydrothiophene 1,1-dioxide, 3-(2-hydroxyethylamino)-2,7-dichloro-2,3-dihydrobenzo[b]thiophene 1,1-dioxide, 3-(6-hydroxyhexylamino)-4-methyl-5-bromo-2,3-dihydrobenzo[b] thiophene 1,1-dioxide, 3-(4-hydroxycyclohexylamino)-2-methyl-5-propyl-2,3-dihydrobenzo[b]thiophene 1,1-dioxide, 3-(3-hydroxy-3-phenylpropylamino)-4,5-dichloro-7-methyl-2,3-dihydro-benzo[b]thiophene 1,1-dioxide, 3-(10-hydroxydecylamino)-2-bromo-5,6-dipentyl-2,3-dihydrobenzo[b]thiophene 1,1-dioxide, 3-(3-hydroxycyclohexylamino)-4-chloro-7-butyl-2,3-dihydrobenzo[b]thiophene 1,1-dioxide, 3-hydroxy-2-phenylethylamino)-5-methyl-7-bromo-2,3-dihydrobenzo[b]thiophene 1,1-dioxide, 3-(4-hydroxybutylamino)-2-bromo-4,5-dimethyl-2,3-dihydrobenzo[b]thiophene 1,1-dioxide, 3-(4-hydroxycyclohexylamino)-4,5,6,7-tetrachloro-2,3-dihydrobenzo[b]thiophene 1,1-dioxide, 3-(8-hydroxyoctylamino)-2-propyl-5,6,7-trimethyl-2,3-dihydrobenzo[b]thiophene 1,1-dioxide, 3-(2-hydroxyethylamino)-2-pentyl-4,7-dibromo-2,3-dihydrobenzo[b]thiophene 1,1-dioxide, and the like.

A preferred subclass of chain extenders of Formula I are those in which X, Y and Z are hydrogen, and R is an open chain alkylene group having 2 to 10, preferably 3 to 10, carbon atoms. Particularly preferred compounds of this subclass are 3-(2-hydroxypropylamino)-tetrahydrothiophene 1,1-dioxide, 3-(3-hydroxypropylamino)tetrahydrothiophene 1,1-dioxide, 3-(6-hydroxyhexylamino)tetrahydrothiophene 1,1-dioxide, and 3-(2-hydroxy-1,1-dimethylethylamino) tetrahydrothiophene 1,1-dioxide.

Another preferred subclass of compounds of Formula I are those in which Y and Z are hydrogen, X is a halogen atom (e.g., chlorine, bromine) and R is an open chain alkylene group having 2 to 10 carbon atoms. Particularly preferred in this subclass are 2-chloro-2-(2-hydroxypropylamino)tetrahydrothiophene 1,1-dioxide, 2-bromo-3-(2-hydroxethylamino)tetrahydrothiophene 1,1-dioxide, and 2-bromo-3-(2-hydroxypropylamino)tetrahydrothiophene 1,1-dioxide.

Still another preferred subclass of compounds of Formula I are those in which X, Y and Z are hydrogen, and R is an open chain alkylene group having 2 to 10 carbon atoms substituted with a phenyl group. Particularly preferred in this subclass is 3-(2-hydroxy-2-phenylethylamino)tetrahydrothiophene 1,1-dioxide.

Yet another preferred subclass of compounds of Formula I is represented by those in which X, Y and Z are hydrogen and R is a cycloalkylene group having 4 to 8 carbon atoms. Particularly preferred in this subclass is 3-(4-hydroxycyclohexylamino)tetrahydrothiophene 1,1-dioxide.

A preferred subclass of chain extending agents of Formula II are those in which $R^1$, $R^2$, $R^3$, $R^4$ and X are hydrogen and $R_a$ is an open chain alkylene group having 2 to 10 carbon atoms. Particularly preferred members of this subclass are 3-(2-hydroxypropylamino)-2,3-dihydrobenzo[b]thiophene 1,1-dioxide, 3-(2-hydroxyethylamino)-2,3-dihydrobenzo[b]thiophene 1,1-dioxide and 3-(6-hydroxyhexylamino)-2,3-dihydrobenzo[b]thiophene 1,1-dioxide.

Another preferred subclass of chemicals of Formula II are those in which $R^1$, $R^2$, $R^3$, $R^4$ and X are hydrogen, and $R_a$ is an open chain alkylene group having 2 to 10 carbon atoms substituted with a phenyl group. A particularly preferred chemical in this subclass is 3-(2-hydroxy-2-phenylethylamino)-2,3-dihydrobenzo[b]thiophene 1,1-dioxide.

To employ the present compounds as chain extending agents for polyurethanes the compounds may simply be substituted at least in part for the conventional chain extending agents in any conventional polyurethane formulation of the kind ordinarily employing a chain extender. The proportions of the present chain extender employed may be the same as in conventional practice and the chain-extending reaction may likewise be carried out under the same conditions as are usually employed in conventional polyurethane chain extension. Polyurethane systems of the so-called one-shot type, or of the prepolymer type, may be employed, and the final product may be foam (either rigid or flexible) or a solid, whether elastomeric or otherwise, including thermoplastic polyurethanes, polyurethane surface coatings, etc. As is well understood by those skilled in the art, polyurethane forming systems conventionally involve a combination of at least one long chain polyol (whether a polyester polyol, a polyether polyol or a polyhydrocarbon polyol) and at least one organic polyisocyanate, whether a diisocyanate or a polyisocyanate of higher functionality, of aliphatic, cycloaliphatic, or aromatic type. The relative proportions of polyol and polyisocyanate may be as in conventional practice appropriate to the particular kind of final product desired and the processing or fabricating method chosen.

The polyether types of polyols employed in making polyurethanes include, as is well known to those skilled in the art, poly(oxyalkylene) glycols [e.g. poly (oxyethylene) glycol, poly(oxypropylene) glycol, poly(oxytetramethylene) glycol, etc.] and higher polyether polyols, such as triols e.g., poly(oxypropylene triol), including polyether polyols of higher functionality than three [e.g., poly(oxypropylene adducts of pentaerythritols) and poly(oxypropylene adducts of sorbitol)]. Mention may be made of such polyether polyols as poly(oxypropylene)-poly(oxyethylene)glycol, poly(oxypropylene) adducts of trimethylol propane, poly(oxypropylene)-poly(oxyethylene)adducts of trimethylolpropane, poly(oxypropylene) adducts of 1,2,6-hexanetriol, poly(oxypropylene)-poly(oxyethylene) adducts of ethylenediamine, poly(oxypropylene) adducts of ethanolamine, and poly(oxypropylene) adducts of glycerine.

The polyester types of polyols used in making polyurethanes are likewise well known in the art and require no detailed description here. It will be understood that they include chain extended polyesters made from a glycol (e.g., ethylene and/or propylene glycol) and a saturated dicarboxylic acid (e.g., adipic acid). By way of non-limiting example there may be mentioned poly(ethylene adipate) glycol, poly(propylene adipate) glycol, poly(butylene adipate) glycol, poly(caprolactone) glycol, poly(ethylene adipate-phthalate) glycol, poly-(neopentyl sebacate) glycol, etc. Small amounts of tri-alcohols such as trimethylolpropane or trimethylolethane may be included in the polyester preparation. Polyester polyols with functionalities of three or more [e.g., glycerides of 12-hydroxystearic acid] are also useful. Suitable polyester polyols include those obtainable by reacting such polyols as 1,4-butanediol, hydroquinone bis(2-hydroxyethyl)ether, ethylene glycol, diethylene glycol, triethylene glycol, propylene glycol, dipropylene glycol, 2-methyl-2-ethyl-1,3-propanediol, 2-ethyl-1,3-hexanediol, 1,5-pentanediol, thiodigylcol, 1,3-propanediol, 1,3-butanediol, 2,3-butanediol, neopentyl glycol, 1,2-dimethyl-1,2-cyclopentanediol, 1,2-cyclohexanediol, 1,2-dimethyl-1,2-cyclohexanediol, glycerol, trimethylol propane, trimethylol ethane, 1,2,4-butanetriol, 1,2,6-hexanetriol, pentaerythritol, dipentaerythritol, tripentaerythritol, anhydroaneaheptitol, mannitol, sorbitol, methylglucoside, and the like, with such dicarboxylic acids as adipic acid, succinic acid, glutaric acid, azelaic acid, sebacic acid, malonic acid, maleic acid, fumaric acid, phthalic acid, isophthalic acid, terephthalic acid, tetrachlorophthalic acid, and chlorendic acid; the acid anhydrides and acid halides of these acids may also be used.

Among the polyhydrocarbyl polyols conventionally employed for making polyurethanes there may be mentioned by way of non-limiting example such materials as poly(butadiene) polyols, poly(butadiene-acrylonitrile) polyols and poly(butadiene-styrene) polyols.

The above polyols typically have a molecular weight of about 180 to 8000.

Conventional polyisocyanates used in polyurethane manufacture include, as is well known, aliphatic polyisocyanates, whether open chain, cycloaliphatic or aralphatic. Examples of aliphatic polyisocyanates conventionally employed are trimethylene diisocyanate, tetramethylene-1,4-diisocyanate, hexamethylene-1,6-diisocyanate, 1-methyl-2,4-and 1-methyl-2,6-diisocyanatocyclohexane and mixtures thereof, p-xylylene diisocyanate and m-xylylene diisocyanate (XDI) and mixtures thereof, 4,4'-diisocyanato-dicyclohexylmethane, isophorone diisocyanate, 2,2,4- and 2,4,4-trimethylhexamethylene diisocyanate, and the like.

Similarly, the aromatic polyisocyanates are suitable and include, by way of non-limiting example, such bodies as 2,4-toluene diisocyanate and 2,6-toluene diisocyanate and mixtures thereof (TDI, including crude and polymeric forms), 4,4'-diphenylmethane diisocyanate (MDI, including crude and polymeric forms), p-phenylene diisocyanate, 2,4,6-tolyene triisocyanate, 4,4'4''-triphenylmethane triisocyanate, 2,2-bis(p-isocyanato-phenyl)-propane, polymeric methylene bis(phenyl-4-isocyanate) (e.g., PAPI), naphthalene-1,5-diisocyanate, 3,3'-dimethyl-4,4'-biphenylene diisocyanate, 3,3'-dimethyoxy-4,4'-biphenylene diisocyanate, 3,3'-diphenyl-4,4'-biphenylene diisocyanate, 4,4'-biphenylene diisocyanate, 3,3'-dichloro-4,4'-biphenylene diisocyanate, and the like. Mixtures of two or more of such diisocyanates may also be used. Triisocyanates typically obtained by the reaction of three moles of an arylene diisocyanate with one mole of triol — for example, the reaction product formed from three moles of tolylene diisocyanate and one mole of hexanetriol or of trimethylol propane, may be employed.

In one important aspect, the invention is directed to an improved flexible resilient polyurethane foam and method of making the same, employing the new chemicals described herein as chain extenders. Thus, it is well known that polyetherpolyol-polyisocyanate foams can be made by reacting a non-linear slightly branched polyether glycol or polyol, a diisocyanate, and a polyfunctional chain extender. The present invention is based in part on the discovery that polyurethane foam having a remarkable combination of desirable physical properties surprisingly results when the new N,N'-bis(1,1-dioxohydrothienyl)-diaminoalkanes are employed as bifunctional chain extenders. The foams of this invention are characterized by high tensile strength, high tear resistance and low compression set. This unique combination of physical properties is largely determined by the unique chain extenders employed.

Formation of the preferred foamed products of this invention may be accomplished in a one-shot system by reacting the polyol with excess polyfunctional isocyanate and the new chain extender of the invention in the presence of water and cell modifying agents, e.g. silicone such as trimethyl end-blocked dimethyl polysiloxanes. The polyfunctional isocyanate is typically present in amount of 5-300%, say 40% by weight of the polyol. The binary chain extender of the invention is frequently present in the one shot foam formulation in amount of 0.5 to 15%, preferably 1 to 10%, by weight of the polyol. The water is employed in amount to react with the isocyanate to liberate sufficient gas (carbon dioxide) to produce a foam of the desired physical characteristics. From 0.6 to 10%, say 4% water (by weight of polyol) will give good results.

The mixing of the constituents in the one-shot system in typically performed at room temperature. The polyol, chain extender of the invention, catalyst, water, flame retardant and other cell-modifying agents (surface active agents) such as trimethyl end-blocked dimethyl polysiloxanes are first mixed and then the polyisocyanate is added with vigorous stirring. The gas forming reaction, the chain extension and the cross linking reactions start simultaneously when the polyisocyanate is added.

Some examples of useful catalysts are N-methylmorpholine, N-ethyl-morpholine, triethyl amine, triethylene diamine (Dabco), N,N'-bis(2-hydroxylpropyl)-2-methyl piperazine, dimethyl ethanol amine, tertiary amino alcohols, tertiary ester amines and the like.

In addition to or in place of water the formulation may include a blowing agent of the kind conventionally employed in making polyurethane foam, usually a volatile organic liquid (e.g. boiling within the range of from 50° to 150°F) such as pentane, trichlorofluoromethane, trichloromethylene, tetrachloroethylene, trichlorotrifluoroethane, trichloroethane, methylene chloride, dibromotetrafluoroethane, carbon tetrachloride, etc.

The resulting one-shot foams of the invention surprisingly are characterized by a unique combination of physical properties such as high tensile strength, high tear resistance, high elongation, good resilience properties and low compression set. These flexible foams find utility as automobile and furniture cushioning materials, pillows, mattresses and carpet underlays.

Another important form of the invention is concerned with solid polyurethanes, particularly those made by the so-called prepolymer technique wherein the polyol is prereacted with an excess of the polyisocyanate, and thereafter the prepolymer is chain-extended or cured, using the bifunctional chain extending agent of the invention. Using liquid prepolymers cast elastomeric (or thermoplastic) articles and coatings having highly useful properties may be made in this way.

The following examples demonstrate the invention.

EXAMPLE 1

This example illustrates the preparation of a typical alkanolaminothiophene dioxide of this invention, namely, 3-(2-hydroxypropylamino)tetrahydrothiophene 1,1-dioxide.

To a 1000 ml round-bottom flask equipped with condenser, thermometer and a stirrer were introduced 118 grams (1.0 mole) of 4,5-dihydrothiophene 1,1-dioxide, 250 ml of 70% by weight aqueous ethanol and 82.5 grams (1.1 moles) of 2-hydroxypropylamine. The reaction mixture was then heated at reflux (80°–85° C) for 4 hours. The solvent and the excess 2-hydroxypropylamine were removed under a reduced pressure. The product, 3-(2-hydroxypropylamine)tetrahydrothiophene 1,1-dioxide obtained was a viscous liquid that became a solid, m.p. 50°–60°C. IR spectrum showed absorptions at 3500 cm$^{-1}$ (OH), at 3300 cm$^{-1}$ (NH), at 1310 cm$^{-1}$ and 1125 cm$^{-1}$(SO$_2$) and at 1080 cm$^{-1}$ (C—O).

Analysis for $C_7H_{15}NO_3S$ (percent):
Calc'd: C, 43.50; H, 7.82; N, 7.25; S, 16.59.
Found: C, 43.32; H, 7.75; N, 7.01; S, 16.39.

EXAMPLE 2

Example 1 was repeated using the thiophene dioxide of Example 1 and substituting 3-hydroxypropylamine for 2-hydroxypropylamine. The resultant product, 3-(3-hydroxypropylamino)-tetrahydrothiophene 1,1-dioxide, was a viscous liquid that became a solid on standing, m.p. 55°–60° C. IR spectrum showed the absorption bands at 3500 cm$^{-1}$(OH), at 3300 cm$^{-1}$ (NH), at 1300 cm$^{-1}$ and 1130 cm$^{-1}$ (SO$_2$) and at 1070 cm$^{-1}$ (C—O—).

Analysis for $C_7H_{15}NO_3S$ (percent):
Calc'd: N, 7.25; S, 16.59.
Found: N, 7.24; S, 15.90.

EXAMPLE 3

Example 1 was repeated using the dioxide of Example 1 and substituting 6-hydroxyhexylamine for 2- hydroxypropylamine. The resultant product, 3-(6-hydroxyhexylamino) tetrahydrothiophene 1,1-dioxide was a viscous liquid and was hygroscopic. The nmr spectrum in $CDCl_3$ showed bands with relative areas in agreement with the structure. The IR spectrum showed absorption at 3520 cm$^{-1}$ (OH), at 3300 cm$^{-1}$ (NH), at 1310 cm$^{-1}$ and 1150 cm$^{-1}$ ($SO_2$), and at 1050 cm$^{-1}$(C—O).

Analysis for $C_{10}H_{21}NO_3S$ (percent): Calc'd: C, 51.03; H, 8.99; N, 5.95; S, 13.62. Found: C, 49.75; H, 8.87; N, 5.82; S, 13.39.

EXAMPLE 4

Example 1 was repeated using the thiophene dioxide of Example 1 but substituting 2-hydroxymethyl-2-propylamine for 2-hydroxypropylamine. The resultant product, 3-(2-hydroxy-1,1-dimethylethylamino)tetrahydrothiophene 1,1-dioxide was a viscous liquid which became solid on standing, mp 90°–95°C. after one recrystallization from a 90/10 volume percent toluene-ethanol solvent mixture. The IR spectrum showed bands at 3500 cm$^{-1}$ (OH), at 3300 cm$^{-1}$ (NH), at 1315 cm$^{-1}$ and 1140 cm$^{-1}$ ($SO_2$) and at 1060 cm$^{-1}$ (CO). The NMR spectrum showed the bands with relative areas in agreement with the structure.

Analysis for $C_8H_{17}NO_3S$ (percent): Calc'd: C, 46.35; H, 8.26; N, 6.75; S, 15.46. Found: C, 45.57; H, 8.14; N, 6.60; S, 15.48.

EXAMPLE 5

Example 1 was repeated using the thiophene dioxide of Example 1 and substituting (2-hydroxy-2-phenyl)ethylamine for 2-hydroxypropylamine. The resultant product 3-(2-hydroxy-2-phenylethylamino)tetrahydrothiophene 1,1-dioxide was a viscous liquid which became solid on standing, and had a melting point of 100°–110°C after one recrystallization from hot toluene. The IR spectrum showed the absorption bands at 3500 cm$^{-1}$ (OH), at 3300 cm$^{-1}$, at 1310 cm$^{-1}$ and 1030 cm$^{-1}$ ($SO_2$), at 1060 cm$^{-1}$(C—O). and at 765 cm$^{-1}$ and 708 cm$^{-1}$ (monosubstituted aromatic). The Nmr spectrum was in agreement with the structure.

Analysis for $C_{12}H_{17}NO_3 S$ (percent): Calc'd: C, 56.45; H, 6.71; N, 5.49; S, 12.55. Found: C, 56.60; H, 6.54; N, 5.60; S, 12.53.

EXAMPLE 6

Example 1 was repeated using the thiophene dioxide of Example 1 and substituting 4-hydroxycyclohexylamine for 2-hydroxypropylamine. The resultant product, 3-(4-hydroxycyclohexylamino)tetrahydrothiophene 1,1-dioxide was obtained as white needles, m.p. 168°–171°C after one recrystallization from a 90/10 volume percent toluene-ethanol solvent mixture.

Analysis for $C_{10}H_{19}NO_3S$ (percent): Calc'd: C, 51.48; H, 8.27; N, 6.00; S, 13.74. Found: C, 51.49; H, 8.10; N, 6.06; S, 13.15.

EXAMPLE 7

Example 1 was repeated using the alkanolamine of Example 1 (2-hydroxypropylamine) but substituting 2-chloro-4,5-dihydrothiophene 1,1-dioxide for the dioxide. The resultant product, 2-chloro-3-(2-hydroxypropylamino)tetrahydrothiophene 1,1-dioxide was a viscous liquid. The IR spectrum showed bands at 3510 cm$^{-1}$ (OH), at 3310 cm$^{-1}$ (NH), at 1320 cm$^{-1}$ and 1130 cm$^{-1}$ ($SO_2$) and at 1050 cm$^{-1}$ (C—O).

Analysis for $C_7H_{14}ClNO_3S$ (percent): Calc'd: Cl, 15.57; S, 14.08. Found: Cl, 15.80; S, 14.57.

EXAMPLE 8

Example 1 was repeated using 2-hydroxyethylamine as the alkanolamine and 2-bromo-4,5-dihydrothiophene 1,1-dioxide as the dioxide. The resultant product, 2-bromo-3-(2-hydroxyethylamino)tetrahydrothiophene 1,1-dioxide was a viscous liquid which became solid on standing, M.P. 87°-89°C. The IR spectrum showed absorptions at 3500 cm$^{-1}$ (OH), at 3310 cm$^{-1}$ (NH), at 1310 cm$^{-1}$ and 1125 cm$^{-1}$ ($SO_2$) and at 1060 cm$^{-1}$(C—O).

Analysis for $C_6H_{12}BrNO_3S$ (percent): Calc'd: C, 27.90; H, 4.68; Br, 30.95; N, 5.42; S, 12.42. Found: C, 27.75; H, 4.55; Br, 30.32; N, 5.28; S, 11.94.

EXAMPLE 9

Example 8 was repeated using the thiophene dioxide of Example 8 but substituting 2-hydroxypropylamine for 2-hydroxyethylamine. The resultant product, 2-bromo-3-(2-hdroxypropylamino)tetrahydrothiophene 1,1-dioxide was a viscous liquid. The IR showed absorptions at 3500 cm$^{-1}$ (OH), at 3310 cm$^{-1}$ (NH), at 1320 cm$^{-1}$ and 1125 cm$^{-1}$ ($SO_2$) and at 1050 cm$^{-1}$ (C—O).

Analysis for $C_7H_{14}BrNO_3S$ (percent): Calc'd: C, 30.89; H, 5.19; Br, 29.36; N, 5.14; S, 11.78. Found: C, 30.99; H, 5.34; Br, 28.72; N, 5.19; S, 11.91.

EXAMPLE 10

Example 8 was repeated using 2-hydroxyethylamine for Example 8 and substituting benzo[b]thiophene 1,1-dioxide for the dioxide. The reaction mixture was heated at reflux overnight (16-20 hours) and the resultant product, 3-(2-hydroxyethylamino)-2,3-dihydrobenzo[b]thiophene 1,1-dioxide was a viscous liquid. The IR spectrum showed absorptions at 3500 cm$^{-1}$ (OH), at 3300 cm$^{-1}$ (NH), at 1300 cm$^{-1}$ and 1125 cm$^{-1}$ ($SO_2$), at 1050 cm$^{-1}$ (C—O) and at 800 cm$^{-1}$ and 765 cm$^{-1}$ (aromatic).

Analysis for $C_{10}H_{13}NO_3S$ (percent): Calc'd: C, 52.84; H, 5.76; N, 6.16; S, 14.16. Found: C, 51.85; H, 5.80; N, 5.95; S, 13.98

EXAMPLE 11

Example 10 was repeated using the thiophene dioxide of Example 10 and substituting 2-hydroxypropylamine for 2-hydroxyethylamine. The resultant product, 3-(2-hydroxypropylamino)-2,3-dihydrobenzo[b]thiophene 1,1-dioxide was a viscous liquid. The IR spectrum showed absorptions at 3510 cm$^{-1}$ (OH), at 3310 cm$^{-1}$ and 1120 cm-1 ($SO_2$), at 1060 cm$^{-1}$(C—O) and at 800 cm$^{-1}$ and 765 cm$^{-1}$ (aromatic).

Analysis for $C_{11}H_{15}NO_3S$ (percent): Calc'd: C, 54.75; H, 6.26; N, 5.80; S, 13.29. Found: C, 54.69; H, 6.32; N, 5.72; S, 13.09.

EXAMPLE 12

Example 10 was repeated using thiophene dioxide of Example 10 and substituting 6-hydroxyhexylamine for 2-hydroxyethylamine. The resultant product 3-(6-hydroxyhexylaminio)-2,3-dihydrobenzo[b]thiophene 1,1-dioxide was a viscous liquid. The IR spectrum showed bands at 3500 cm$^{-1}$ (OH), at 3300 cm$^{-1}$ (NH), at 1300 cm$^{-1}$ and 1125 cm$^{-1}$ ($SO_2$), at 1055 cm$^{-1}$ (C—O) and at 880 cm$^{-1}$ and 765 cm$^{-1}$ (aromatic).

Analysis for $C_{14}H_{21}NO_3S$ (percent): Calc'd: C, 59.33; H, 7.47; N, 4.94; S, 11.31. Found: C, 59.47; H, 7.49; N, 5.06; S, 10.54.

EXAMPLE 13

Example 10 was repeated using the thiophene dioxide of Example 10 and substituting (2-hydroxy-2-phenyl)ethylamine for 2-hydroxyethylamine. The resultant product, 3-(2-hydroxy-2-phenylethylamino)-2,3-dihydrobenzo[b]thiophene 1,1-dioxide obtained as white solid had a melting point 123°–126°C. The IR spectrum showed absorptions at 3500 cm$^{-1}$ (OH), at 3320 cm$^{-1}$ (NH), at 1310 cm$^{-1}$ and 1110 cm$^{-1}$ (SO$_2$), at 1060 cm$^{-1}$ (C—O), and at 770 cm$^{-1}$ and 704 cm$^{-1}$ (aromatic).

Analysis for $C_{16}H_{17}NO_3S$ (percent): Calc'd: C, 63.33; H, 5.65; N, 4.61; S, 10.56. Found: C, 63.07; H, 5.41; N, 4.34; S, 10.58.

As indicated above, chain extenders of this invention find use in the "one-shot" system of solid foamed polyurethanes. In this system, the mixing of the constituents is typically performed at room temperatures. The polyol (polyester polyol, polyether polyol or polyhydrocarbon polyol), chain extender, catalyst, water, flame retardant and other cell-modifying agents (surface active agents), are first mixed and then the polyisocyanate is added with vigorous stirring. The gas forming reaction, the chain extension and the cross-linking reactions start simultaneously when the polyisocyanate is added.

The formation of foamed products is accomplished in the one-shot system by reacting the polyol with a slight excess, typically about 5 to 10 equivalent weight percent excess, of polyfunctional isocyanate in the presence of water and cell modifying agents, e.g. silicones such as trimethyl end-blocked dimethyl polysiloxanes. The polyfunctional isocyanate is typically present in amount of 5–300%, say 40%, by weight of the polyol. The water should be present in amount to react with the isocyanate to liberate sufficient gas (carbon dioxide) to produce a foam of the desired physical characteristics. From 0.5 to 10%, say 3% water (by weight of polyol), will give good results. Some examples of useful catalysts are N-methylmorpholine, N-ethylmorpholine, triethyl amine, triethylene diamine (Dabco, trademark), N,N'-bis(2-hydroxypropyl)-2-methyl piperazine, dimethyl ethanol amine, tertiary amino alcohols, tertiary ester amines and the like. For further details on the formulation of polyether-polyol based one shot foam formulations reference may be had to copending application Ser. No. 336,842 of Mao and Bakker, filed Feb. 28, 1973, the disclosure of which is hereby incorporated herein by reference. An example of this form of the invention is as follows:

EXAMPLE 14

This example demonstrates the use of two novel compounds of this invention as binary chain extenders in the preparation of foamed polyurethane structures using a conventional high resiliency foam formulation. For comparison purposes, the most widely used chain extender 4,4'-methylene-bis-(o-chloroaniline), which is commonly designated by the code letters MOCA, was also used. The formulations and results are tabulated in Table I.

It should be noted that the polyurethane foamed structures A and B made with the novel compounds of this invention exhibit a unique combination of physical properties such as high tensile strength, high tear resistance, high elongation and low compression set. Tensile, tear and elongation in A are superior to C at somewhat higher but still acceptable compression, tear and elongation in B are superior to C at substantially the same compression.

In Table I the formulations are expressed as parts by weight. The polyol may be a polypropylene glycol triol of 4700 molecular weight made from propylene glycol and endcapped with 20 to 80% ethylene oxide (Voranol 4701; trademark). The Ex. 1 compound is the binary chain extender prepared in Example 1 above; the Ex. 11 compound is that prepared in Example 11 above. The fire retardant may be tris(2,3-dibromopropyl)phosphate (Firemaster T23P; trademark). TDI is toluene diisocyanate (80% 2,4-isomer and 20% 2,6-isomer, by weight). The rise time is expressed in seconds, the density in pounds per cubic foot, the tensile in pounds per square inch, the tear is pounds per linear inch, and the elongation and set in percent. All the properties were determined according to ASTM D-2406-68 procedures.

In each formulation in Table I the polyol, chain extender, catalyst, water, flame retardant and cell modifying agent (siloxane) are first mixed at room temperature and then the polyisocyanate is added (also at room temperature) with vigorous stirring; the liquid mixture quickly foams up and solidifies, forming a resilient polyurethane foam.

Table 1

| One-Shot Polyurethane Foam Formulations | | | |
|---|---|---|---|
| | A | B | C |
| Polyol | 100 | 100 | 100 |
| Ex. 1 compound | 5 | — | — |
| Ex. 11 compound | — | 5 | — |
| MOCA | — | — | 4 |
| Water | 3.6 | 3.6 | 3.6 |
| Fire retardant | 3.0 | 3.0 | 3.0 |
| Catalysts | 1.4 | 1.4 | 1.4 |
| Siloxane | 0.05 | 0.05 | 0.05 |
| TDI | 47.1 | 46.1 | 52.0 |
| Results | | | |
| Rise Time | 90 | 95 | 95 |
| Density | 2.01 | 1.91 | 2.10 |
| Tensile | 19.75 | 17.48 | 17.5 |
| Tear | 3.6 | 2.79 | 1.76 |
| Elongation | 292 | 245 | 215 |
| Compression set | | | |
| 50% | 15.6 | 12.9 | 9.0 |
| 75% | 17.8 | 10.4 | 10.0 |

EXAMPLE 15

This example illustrates the use of the 3-(hydroxyhydrocarbylsecondaryamino)-dihydrobenzo[b]thiophene 1,1-dioxides as binary chain extenders for castable solid polyurethanes made from polyester-based prepolymers. In this system the prepolymer is first prepared by reacting a predetermined excess of a diisocyanate with a polyester polyol such as polyethylene adipate diol and the resulting prepolymer is reacted with the binary extender at elevated temperature (e.g., 70°C). The resultant reaction mixture is then poured into a mold, cured for about 1.5 hours at about 125°C and conditioned in air at 25°C and 50% relative humidity for 14 days before testing. This procedure may be followed using as the prepolymer an MDI-polyester (e.g., adipic acid-ethylene glycol polyester) prepolymer containing about 6.3% free isocyanate, having an amine equivalent of about 665 and a viscosity at 212°F of 10 poises, and the compound of Example 11 as the binary chain extender.

The prepolymer (130 gms) was mixed with the chain extender of Example 11 (21 gms) at 70°C and poured into two open top 7.5 × 7.5 × 0.1 inch polytetrafluoroethylene (Teflon; trademark) coated molds which were heated and kept at 110°C. The molds were then closed and the cast samples were cured in a heated hydraulic press using contact pressure for 1.5 hours at 125°C. After cure, the samples were cooled to room temperature, removed from the mold and conditioned in air at 25°C and 50% relative humidity for 14 days before testing. The physical properties of the solid, rubbery thermoplastic polyurethane were as follows:

| | |
|---|---|
| Durometer, Shore "A" | = 63 |
| Tensile Strength, psi | = 4210 |
| Tear Strength, lbs/in | = 308 |
| Stress at 100% Elongation, psi | = 270 |
| % Elongation | = 560 |
| Optical Properties | = Transparent |
| Pot Life, minutes | = 20 |

The Shore hardness was determined according to ASTM D 2240-68. The tensile strength and elongation were determined in a Scott machine following ASTM D 412-68, using a sample 0.10 inch thick and a jaw separation rate of 20 inches per minute. The tear strength was determined by the procedure of ASTM 624-54 but using a sample measuring 3 inches by 1 inch which was died out from a sheet of stock 0.10 inch thick with a 2 inch slit extending lengthwise from one end. The two legs were put in the jaws of a Scott tester model L and elongated until torn apart. The force required to accomplish this was recorded. The stress at 100% elongation was determined from autographic stress-strain measurements. A 0.10 inch thick sample is died out into a ring, 3 cm. inner diameter, 3.5 cm. outer diameter, placed around pullup rotating at 200 rpm, and elongated at a rate of 10 inches per minute.

EXAMPLE 16

This example further illustrates the preparation of a polyurethane foam made with 3-(2-hydroxypropylamino) tetrahydro-thiophene 1,1-dioxide (designated CE-1 in Table II) as the chain extender.

In Table II, the amounts of ingredients are listed in parts by weight; the polyol is the polyether polyol described in Example 14; NEM is N-ethylmorpholine. To a 16 ounce paper cup, all of the ingredients in formulation 16 of Table II except the TDI were added. This was mixed for approximately 2 minutes and then the TDI added. This combination was then mixed for approximately 10 seconds and poured into a 15 × 15 × 4 inch aluminum mold which was about 110°F. This was cured for 20 minutes at 250°F. and the resultant sample aged 1 week at room temperature before the physical test were run, with the results shown in Table II.

EXAMPLE 17

Example 17 in Table II is the same as Example 16 except that the level of the fire retardant T-23P was raised from 3 parts to 5 parts.

EXAMPLE 18

This example illustrates the preparation of the polyurethane foam made with the chain extender of Example 11, identified as CE-11 in Table II, namely, 3-(2-hydroxypropylamino)-2,3-dihydrobenzo[b]thiophene 1,1-dioxide. This example was made the same way as Example 16.

EXAMPLE 19

This example was the same as Example 18 except that the T-23P level was increased from 3 to 5 parts.

EXAMPLE 20

This example illustrates the preparation of polyurethane foam made with 3-(2-hydroxyethylamino)tetrahydrothiophene 1,1-dioxide as the chain extender, identified as CE-20 in Table II. This example was prepared in the same manner as Example 16.

EXAMPLE 21

This example is the same as Example 20 except that the T-23P level was increased from 3 to 5 parts.

EXAMPLE 22

This example is the same as Example 20 except that instead of using a 100% TDI system, a 95/5 blend based on equivalents was used of TDI and polymeric MDI (PAPI 901; trademark, polymethylene polyphenylisocyanate).

EXAMPLE 23

This example, which is outside the invention, employs MOCA as the chain extender and is included so that it may be used as a comparison between the chain extenders of the invention and a conventionally used chain extender. It was prepared in the same manner as Example 22. Tear strength and elongation, which are the more important properties for flexible polyurethane foams, are superior in the foams made with the chain extenders of the invention, while achieving a desirable value of less than 20% for the compression set.

TABLE II

| Material | POLYURETHANE FOAMS | | | | | | | |
|---|---|---|---|---|---|---|---|---|
| | 16 | 17 | 18 | 19 | 20 | 21 | 22 | 23 |
| Voranol 4701 | 100 | 100 | 100 | 100 | 100 | 100 | 100 | 100 |
| CE-1 | 5.0 | 5.0 | — | — | — | — | — | — |
| CE-11 | — | — | 5.0 | 5.0 | — | — | — | — |
| CE-20 | — | — | — | — | 5.0 | 5.0 | 5.0 | — |
| MOCA | — | — | — | — | — | — | — | 5.0 |
| Water | 3.6 | 3.6 | 3.6 | 3.6 | 3.6 | 3.6 | 3.6 | 3.6 |
| T-23P | 3.0 | 5.0 | 3.0 | 5.0 | 3.0 | 5.0 | 3.0 | 3.0 |
| Amine Catalysts | | | | | | | | |
| Dabco | 0.50 | 0.50 | 0.50 | 0.50 | 0.50 | 0.50 | 0.60 | 0.60 |
| NEM | 0.75 | 0.75 | 0.75 | 0.75 | 0.75 | 0.75 | 0.75 | 0.75 |
| Niax | 0.15 | 0.15 | 0.15 | 0.15 | 0.15 | 0.15 | 0.15 | 0.15 |

TABLE II—Continued

| Material | POLYURETHANE FOAMS | | | | | | | |
|---|---|---|---|---|---|---|---|---|
| | 16 | 17 | 18 | 19 | 20 | 21 | 22 | 23 |
| Tin Catalyst T-12 | — | — | — | — | — | — | 0.03 | .0075 |
| DC-200 | .05 | .05 | .05 | .05 | .05 | .05 | .05 | .05 |
| TDI | 47.0 | 47.0 | 46.1 | 46.1 | 47.0 | 47.0 | 44.6 | 40.2 |
| PAPI 901 | — | — | — | — | — | — | 3.6 | 0.8 |
| Isocyanate Index | 105 | 105 | 105 | 105 | 105 | 105 | 105 | 105 |
| Tensile | 19.75 | 20.61 | 17.48 | 19.06 | 15.27 | 14.40 | 18.74 | 22.03 |
| Tear | 3.60 | 3.34 | 2.79 | 3.06 | 2.76 | 3.12 | 1.94 | 1.87 |
| Elongation | 292 | 265 | 245 | 262 | 227 | 212 | 150 | 139 |
| Compression Set | | | | | | | | |
| 50% | 15.60 | 16.61 | 12.98 | 12.18 | 12.92 | 17.11 | 13 | 9.4 |
| 75% | 17.82 | 17.26 | 10.37 | 12.93 | 12.04 | 12.37 | 11.5 | 11.4 |

I claim:

1. A 3-(hydroxyhydrocarbylsecondary-amino)-2,3-dihydrobenzo(b) thiophene 1,1-dioxide of the following formula

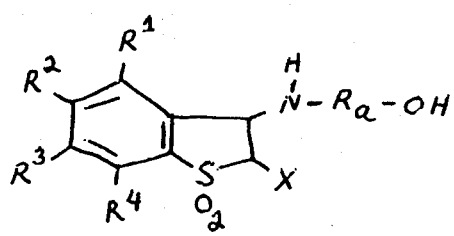

wherein

X may be hydrogen, an alkyl group having 1 to 5 carbon atoms or a halogen atom, $R_a$ may be (1) an open chain alkylene group having 2 to 10 carbon atoms (2) an open chain alkylene group having 2 to 10 carbon atoms substituted with one or more phenyl groups, or (3) a cycloalkylene group having 4 to 8 carbon atoms, the hydroxyl group being attached to a carbon atom of $R_a$ that is separated from the secondary amino nitrogen atom by at least one carbon atom, and $R^1$, $R^2$, $R^3$ and $R^4$ are the same or different and are hydrogen, an alkyl group having 1 to 5 carbon atoms, or halogen.

2. A new chemical compound as in claim 1, in which $R^1$, $R^2$, $R^3$, $R^4$ and X and hydrogen and $R_a$ is an open chain alkylene group having 2 to 10 carbon atoms.

3. A new chemical compound as in claim 1, in which $R^1$, $R^2$, $R^3$, $R^4$ and X are hydrogen and $R_a$ is an open chain alkylene group having 2 to 10 carbon atoms substituted with a phenyl group.

4. A chemical as in claim 1 which is 3-(2-hydroxypropylamino)-2,3-dihydrobenzo[b]thiophene 1,1-dioxide.

5. A chemical as in claim 1 which is 3-(2-hydroxyethylamino)-2,3-dihydrobenzo[b]thiophene 1,1-dioxide.

6. A chemical as in claim 1 which is 3-(6-hydroxyhexylamino)-2,3-dihydrobenzo[b]thiophene 1,1-dioxide.

7. A chemical as in claim 1 which is 3-(2-hydroxy-2-phenylethylamino)-2,3-dihydrobenzo[b]thiophene 1,1-dioxide.

* * * * *